US006773454B2

United States Patent
Wholey et al.

(10) Patent No.: US 6,773,454 B2
(45) Date of Patent: Aug. 10, 2004

(54) TAPERED ENDOVASCULAR STENT GRAFT AND METHOD OF TREATING ABDOMINAL AORTIC ANEURYSMS AND DISTAL ILIAC ANEURYSMS

(76) Inventors: Michael H. Wholey, 19407 Straus, San Antonio, TX (US) 78256; Mark H. Wholey, 816 Woodland Ave., Oakmont, PA (US) 15139; Boulos Toursarkissian, 5760 Verbena St., San Antonio, TX (US) 78240

( * ) Notice: Subject to any disclaimer, the term of this patent is extended or adjusted under 35 U.S.C. 154(b) by 0 days.

(21) Appl. No.: 09/753,119

(22) Filed: Jan. 2, 2001

(65) Prior Publication Data

US 2002/0052643 A1 May 2, 2002

Related U.S. Application Data

(60) Provisional application No. 60/222,617, filed on Aug. 2, 2000.

(51) Int. Cl.[7] .................................................. A61F 2/06
(52) U.S. Cl. ...................... 623/1.15; 623/1.16; 623/1.24
(58) Field of Search ................................ 623/1.1, 1.24, 623/1.11, 1.15, 1.16; 606/190–200

(56) References Cited

U.S. PATENT DOCUMENTS

| | | | |
|---|---|---|---|
| 5,156,620 A | * 10/1992 | Pigott | ........................ 623/1.25 |
| 5,527,355 A | * 6/1996 | Ahn | ........................... 623/1.36 |
| 5,676,696 A | * 10/1997 | Marcade | .................... 623/1.35 |
| 5,683,449 A | 11/1997 | Marcade | |
| 5,716,393 A | 2/1998 | Lindenberg et al. | |
| 5,855,597 A | 1/1999 | Jayaraman | |
| 5,876,432 A | * 3/1999 | Lau et al. | .................... 606/191 |
| 5,891,191 A | 4/1999 | Stinson | |
| 5,906,641 A | 5/1999 | Thompson et al. | |
| 5,916,264 A | 6/1999 | Von Oepen et al. | |
| 5,922,019 A | * 7/1999 | Hankh et al. | ................ 606/198 |
| 5,925,075 A | 7/1999 | Myers et al. | |
| 5,957,974 A | 9/1999 | Thompson et al. | |
| 6,001,123 A | 12/1999 | Lau | |
| 6,010,529 A | 1/2000 | Herweck et al. | |
| 6,015,431 A | 1/2000 | Thornton et al. | |
| 6,030,415 A | * 2/2000 | Chuter | ....................... 604/191 |
| 6,039,755 A | 3/2000 | Edwin et al. | |
| 6,042,605 A | 3/2000 | Martin et al. | |
| 6,120,534 A | 9/2000 | Ruiz | |

OTHER PUBLICATIONS

Sellers et al. "Percutaneous endovascular graft repair of common iliac aneurysm, our three year experience". Abstract #15, BIRS Annual General Meeting, Nov. 1998.*

* cited by examiner

Primary Examiner—Corrine McDermott
Assistant Examiner—Kamrin Landrem
(74) Attorney, Agent, or Firm—Lara A. Northrop, Esq.; Alan G. Towner, Esq.; Pietragallo, Bosick & Gordon

(57) ABSTRACT

An endovascular stent graft is provided for use in treating abdominal aortic aneurysms. The endovascular stent has a tapered section which allows it to accommodate markedly large aortas such as the abdominal aorta and still connects to standard modular aortic stent grafts. Methods of utilizing the stent to treat abdominal aortic aneurysms and distal iliac aneurysms are also provided.

49 Claims, 10 Drawing Sheets

TAPERED ENDOVASCULAR STENT GRAFT AND METHOD OF TREATING ABDOMINAL AORTIC ANEURYSMS AND DISTAL ILIAC ANEURYSMS

CROSS REFERENCE TO RELATED APPLICATION

This application claims the benefit of U.S. Provisional Application Serial No. 60/222,617, filed Aug. 2, 2000.

BACKGROUND OF THE INVENTION

1. Field of Invention

The present invention relates to an endovascular stent and, more specifically, to a endovascular stent having a cephalic section with a cross-sectional area, a caudal section with a cross-sectional area that is smaller than the cephalic section cross-sectional area, and a tapered mid-section disposed therebetween. Methods of utilizing the stent to treat abdominal aortic aneurysms and distal iliac aneurysms are also provided.

2. Background Information

There have been numerous patents upon stents and endovascular stent grafts. When a person develops abdominal aortic aneurysm, there is a high risk of rupture. Treatment options include surgery or endovascular stent graft placement.

One of the limitations of stent graft placement has been the size of the abdominal aorta at the level of the neck or the region just distal to the renal arteries. Typically, the stent is limited to a 28 mm diameter and must be placed in a portion of the abdominal aorta having a similar diameter. There is one product currently available to accommodate larger aortas, but you need an expanded inventory to accommodate stents having the larger sizes. A second problem with larger stent diameters is the delivery device needed to advance the system. In order to advance most stent systems, you will need at least 7–8 mm diameter of the iliac arteries.

SUMMARY OF THE INVENTION

This invention provides the means for treating abdominal aortic aneurysms with standard modular endovascular stent graft systems. The invention is a tapered stent graft system that allows it to be joined with a secondary, standard modular endovascular stent graft system. The cephalic end, towards the patient's head, includes a cephalic section forming a cephalic plenum. The cephalic section has a cross-sectional area. The caudal end, towards the patient's feet, includes a caudal section forming a caudal plenum. The caudal section has a smaller cross-sectional area than the cephalic section. Between the cephalic section and the caudal section is a tapered mid-section.

The endovascular stent is composed of self expanding stent material to provide constant expansion of the cuff against the aortic wall and the adjoining stent graft system. The graft material attached to the stent will be compatible with endovascular graft material used in arterial treatment.

On the cephalic end, there are a plurality of struts that are not covered with graft material. The remaining portion, or approximately ⅘, of the endovascular stent is covered with a graft material attached to the underlying stent. The purpose of the exposed or uncovered cephalic end is to allow possible expansion of the system against the aorta and cross important origins, such as the renal arteries. This provides the necessary anchor for the extension cuff. It will be capable of expanding up to a diameter of 35 mm or higher if needed.

At the caudal end of the endovascular stent, the diameter of the endovascular stent decreases significantly. The area of the covered stent between the larger cephalic and narrower caudal is a smooth but quick transition or taper. The narrow caudal end will extend a certain distance to allow other modular stent graft systems to be attached. The narrow caudal end may have a flare or bell-bottom end to facilitate re-canalization.

At the tips and mid section of the endovascular stent will be a radiopaque markers to help visualize the cephalic and caudal ends under fluoroscopy.

It is an object of this invention to provide an endovascular stent which includes a generally cylindrical cephalic section defining a cephalic lumen and having a cross-sectional area, a tapered mid-section, caudal section defining a caudal lumen and having a cross-sectional area, the mid-section disposed between, and attached to both the cephalic section and the caudal section, and wherein the cephalic cross-sectional area is larger than the caudal cross-sectional area and the mid-section tapers from the cephalic cross-sectional area to the caudal cross-sectional area.

It is a further object of this invention to provide a method of using a endovascular stent having a different sized cylindrical end sections and a tapered section therebetween for treating an abdominal aortic aneurysm, wherein the method includes the steps of: providing a collapsible endovascular, collapsing the endovascular stent into a collapsed configuration; inserting the endovascular stent into a patient via a vascular sheath to a location within the abdominal aorta adjacent a abdominal aortic aneurysm, expanding the endovascular stent to an expanded configuration wherein the cephalic section engages the abdominal aorta and the caudal section extends into the abdominal aortic aneurysm.

It is a further object of this invention to provide a method of using a endovascular stent having a different sized cylindrical end sections and a tapered section therebetween for treating a distal iliac aneurysm, wherein the method includes the steps of: providing a collapsible endovascular, inserting the endovascular stent into a patient via a vascular sheath to a location within an iliac artery adjacent to a iliac aneurysm and expanding the endovascular stent to an expanded configuration wherein the flared section engages the iliac artery.

DESCRIPTION OF FIGURES

A full understanding of the invention can be gained from the following description of the preferred embodiments when read in conjunction with the accompanying drawings in which.

DETAILED DESCRIPTION OF A PREFERRED EMBODIMENT

Figure 1:
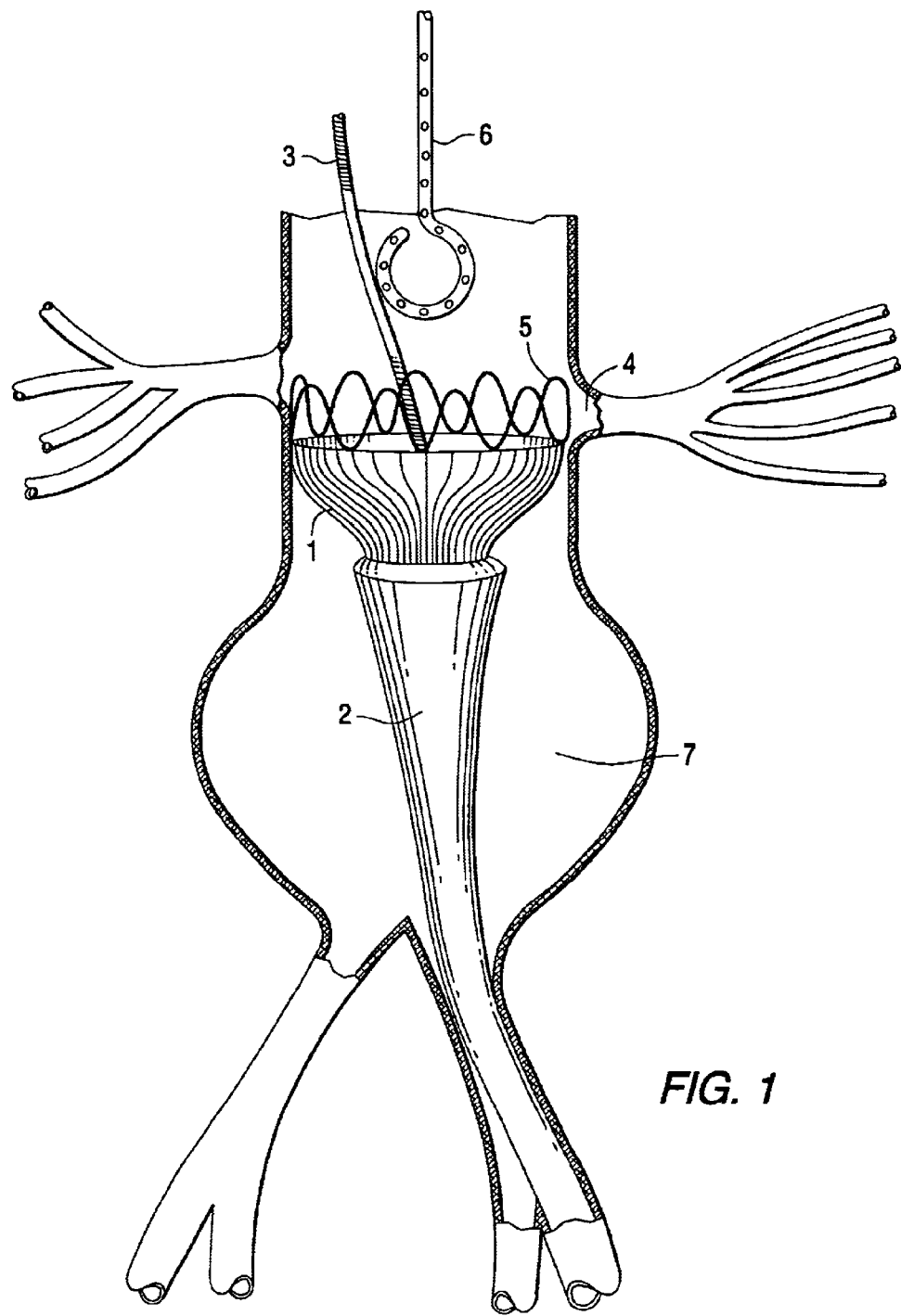
FIG. 1 is an illustration of the endovascular stent being deployed at the level of the renal arteries. The endovascular stent is shown in a cross-sectional view of the human abdominal aorta.

As shown in FIG. 1, an endovascular stent 1 is inserted, in a collapsed configuration (as is known in the art and as described below), through a vascular sheath 2 over a guidewire 3 into a position of the abdominal aorta at the level of the renal artery origins 4. An uncovered stent section 5 is placed at the level of the renal artery origin 4. A diagnostic catheter 6 is placed from above, helping to provide angiographic images of the placement procedure. The delivery sheath 2 is then pulled back, exposing endovascular stent 1 in the abdominal aortic aneurysm 7.

Figure 2:
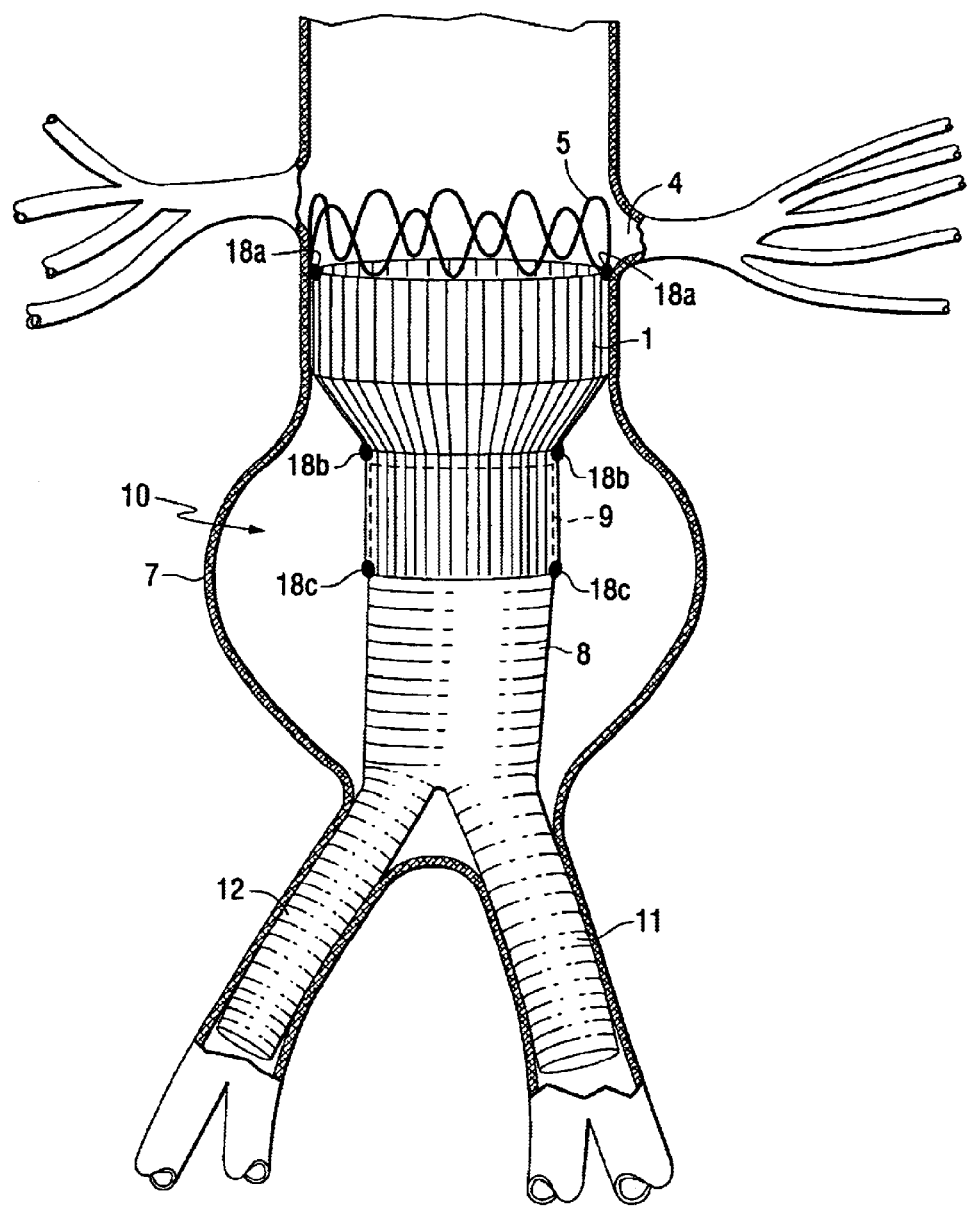
FIG. 2 is an illustration of the endovascular stent fully deployed and attached to another modular designed stent graft system. The endovascular stent is shown in a cross-sectional view of the human abdominal aorta.

As shown in FIG. 2, the endovascular stent 1 is part of a stent system 10 which includes the endovascular stent 1 and at least one modular stent graft 8. After the endovascular stent 1 is in place within the abdominal aorta, the modular stent graft 8 can be advanced and attached to the caudal lumen 16 (described below) of endovascular stent 1. The caudal lumen 16 will overlap the modular stent graft 8 to provide anchoring support. The modular stent graft 8 will have a medial 11 and lateral limb 12 structured to be disposed within the iliac artery. Once in place, the modular stent graft 8 will help exclude flow into the aortic aneurysm 7.

Figure 3:
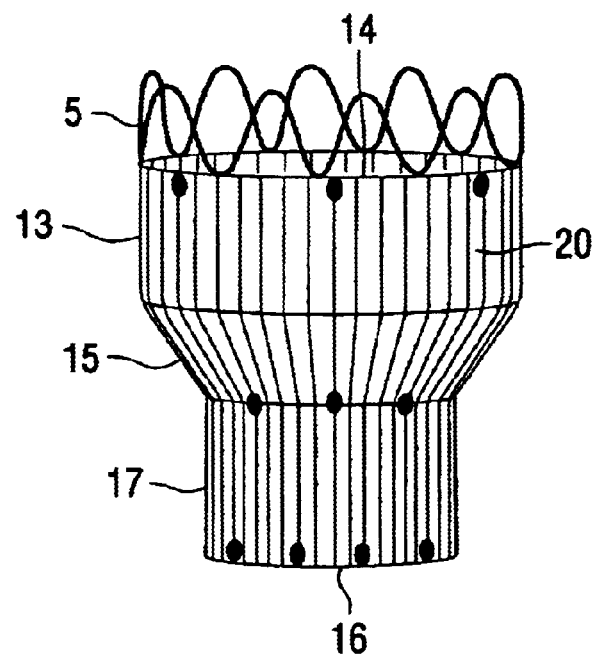
FIG. 3 is slightly obliqued, lateral view of the endovascular stent with the graft material in place.

As shown in FIG. 3, there are four main sections to the endovascular stent 1. First, there is a section having a plurality of metallic self-expandable struts 5 which are not covered with graft material. The struts 5, which expand against the aorta, may be disposed over important artery origins without occluding them. The next section of the endovascular stent 1 is the cephalic section 13. The cephalic section 13 includes a covering 20 (described below) which forms a cephalic lumen 14. The cephalic lumen 14 defines a flowpath which is continuous with the aorta and the remaining sections of the endovascular stent 1. This cephalic section 13 along with the uncovered strut segment 5 has the largest cross-sectional area of the invention. Preferably, the endovascular stent 1 has a generally circular shape and the diameter of the cephalic section 13, in the expanded configuration, is between about 28 mm and 35 mm. The cross-sectional area of the cephalic section 13 is preferably between about 800 to 1,200 mm$^2$. The diameter of the cephalic section 13 is, preferably, constant. Thus, generally the entire length of the cephalic section 13 will contact the abdominal aorta. By virtue of an extended contact area provided by the generally cylindrical cephalic section 13, the risk of endoleaks is reduced.

The next section of the endovascular stent 1 is the mid-section 15. The mid-section 15, which includes the covering 20 (described below) tapers quickly from the diameter of the cephalic lumen 14 to the smaller diameter of the caudal lumen 16 (described below). The mid section further defines the flowpath and is continuous with the cephalic lumen 14. The last section is the caudal section 17. The caudal section 17 also includes the covering 20 (described below) and defines a caudal lumen 16. The caudal lumen 16 further defines the flowpath and is continuous with the mid-section flowpath. The caudal section 17 is structured to engage the modular stent graft 8. Preferably, the diameter of the caudal section 17, in the expanded configuration, is between about 22 mm and 24 mm. The cross-sectional area of the caudal section 17 is preferably between about 300 to 600 mm$^2$.

Figure 4:
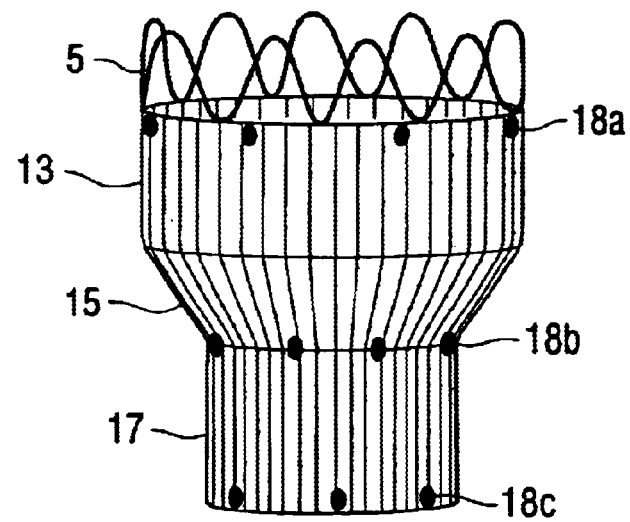
FIG. 4 is a lateral cross-sectional view of the endovascular stent.

As shown in FIG. 4, to aid in placement of the endovascular stent 1, there are a plurality of radiopaque markers 18a, 18b, and 18c along the borders between sections the of the endovascular stent 1. That is, radiopaque markers are disposed between the strut section 5 and the cephalic section 13, between the cephalic section 13 and the mid-section 15, and between the mid-section 15 and the caudal section 17.

The endovascular stent 1 is composed, generally, of two materials: a memory metal, such as nitinol and a covering 20, such as polytetrafluoroethylene, that is structured to promote proper cell growth. The metal forms a frame 19 that is structured to shift between an expanded configuration and a collapsed configuration. The struts 5 may be integral to the frame 19. Over the frame 19, except for the strut section 5, is the covering 20 of vascular graft-type material. The covering 20 is structured to prevent leakage, rupture of disconfiguration. The covering 20 may be disposed either inside or outside the frame 19.

Figure 5:
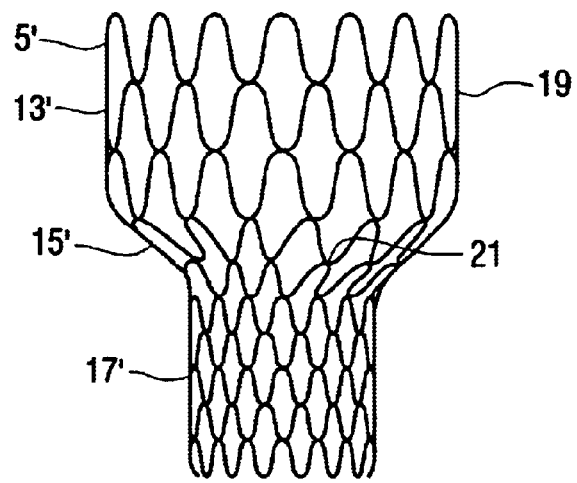
FIG. 5 is a lateral cross-sectional view of the endovascular stent with the graft material removed revealing the underlying stent itself.

As shown in FIGS. 5–8, there can be several different types of construction for the frame 19. In FIG. 5, the covering 20 has been removed from the cephalic section 13, mid-section 15 and caudal section 17 to show an interlocking frame 21. The interlocking frame 21 includes undulating members 21' having a generally U-shape. The U-shaped members overlap each other in a forward and backward manner along the longitudinal axis. The undulating members 21' crisscross along a plurality of longitudinal axis. When so configured, the frame 21 is structured to have an expanded configuration and a collapsed configuration. When the frame 21 is in the expanded configuration, the frame 21 creates a sufficient outward radial force at its cephalic end to ensure complete sealing against the vessel wall and sufficient inward radial strength at its caudal end to ensure complete sealing against the modular stent graft 8.

Figure 6:
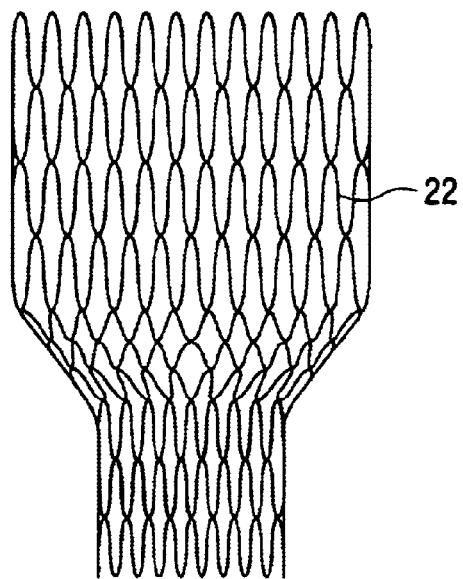
FIG. 6 is a lateral cross-sectional view of the endovascular stent with the graft material removed revealing the underlying stent, which has a closer and tighter pattern.
Figure 7:
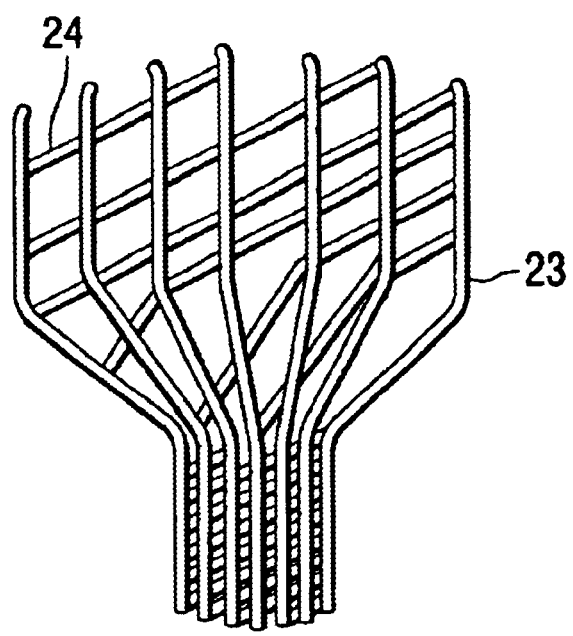
FIG. 7 is a lateral cross-sectional view of the endovascular stent with the graft material removed revealing a framework of vertical struts and ribs providing the metallic structure of the endovascular stent.
Figure 8:
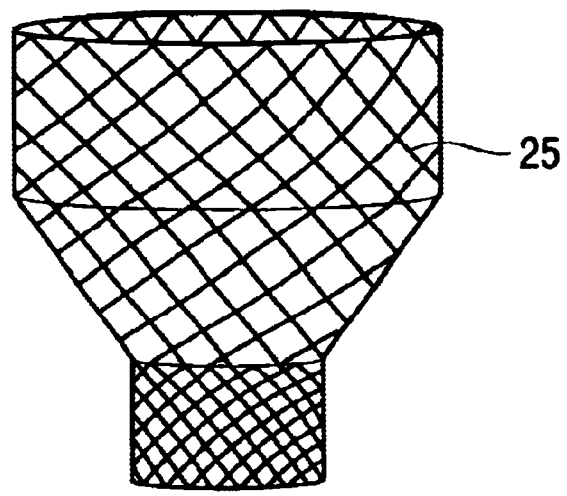
FIG. 8 is a lateral cross-sectional view of the endovascular stent with the graft material removed revealing a cross weave pattern of metal strands creating the framework of the endovascular stent.

An alternate embodiment of the frame 22 is shown in FIG. 6. In this embodiment, undulating metal structure of the frame 22 has a tighter and smaller pattern allowing for more strength. Another embodiment of the frame 23 is shown in FIG. 7. In this embodiment 23, there are a series of longitudinally-placed struts 24a connected together by a plurality of interconnecting ribs 24b. Another embodiment of the frame 25 is shown in FIG. 8. In this embodiment, the frame 25 includes a pattern of overlying wires in a weave-like pattern.

Figure 9:
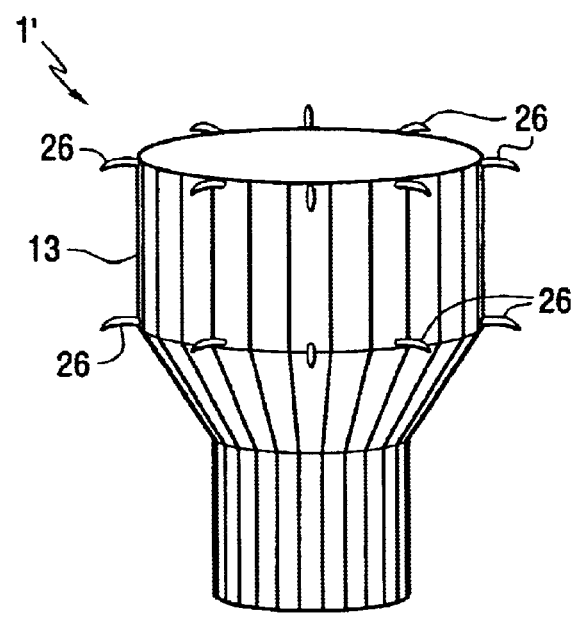
FIG. 9 is a lateral oblique view of the endovascular stent with the hooks placed along the cephalic segment outer diameter.
Figure 10:
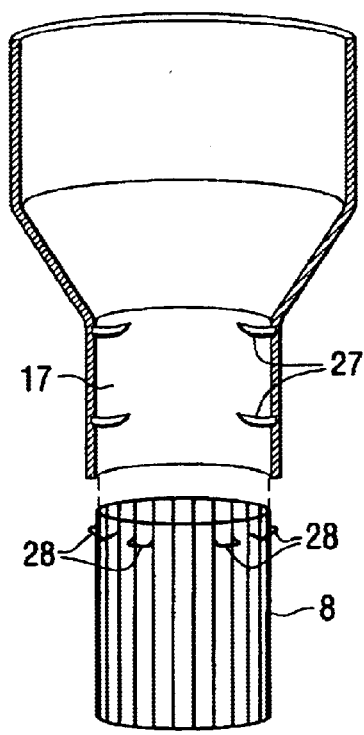
FIG. 10 is a lateral cross-sectional view of the endovascular stent with the graft material removed revealing internal hooks on the inside of the caudal segment and with a oblique view of the coaxial stent graft system in attachment devices along its outer diameter.

Another embodiment of the endovascular stent 1' is shown in FIG. 9. In this embodiment, there are no struts. Instead, a plurality of hooks 26 are located along the cephalic section 13 outer diameter. The hooks 26 provide a means for anchoring the endovascular stent 1. Similarly, as shown in FIG. 10, an internal attachment means, such as internal hooks 27, can be provided in the internal diameter of the caudal section 17 to insure stronger anchoring of the modular stent graft 8. The modular stent graft 8 may include attachment points corresponding to the internal hooks 27.

Figure 11:
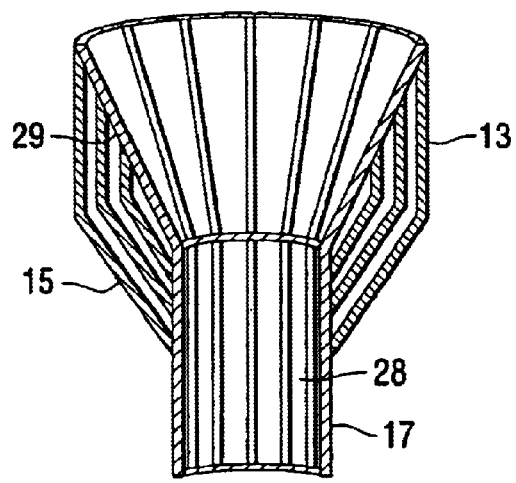
FIG. 11 is a lateral cross-sectional view of the endovascular stent with the graft material removed revealing an extension of the caudal segment allowing for more space for placement of a coaxial stent graft system.

As shown in FIG. 11, the length of the caudal section 17 may be lengthened with an extension piece 28. Such an extension 28 will provide additional landing space for the modular stent graft 8, insuring better anchoring. The extension piece extends from the caudal section 17 towards the cephalic section 13. Additionally, a second, internal cone shaped wall 29 connecting this caudal section 17 with the cephalic section 13 is required to provide smooth laminar flow.

Figure 12:
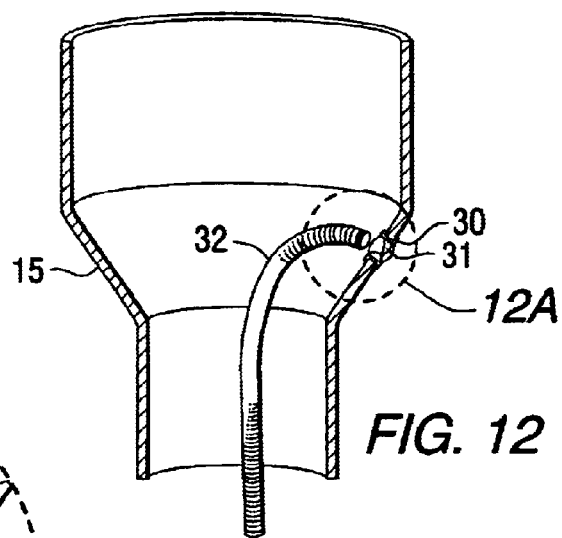
FIG. 12 is a lateral cross-sectional view of the endovascular stent with the graft material removed revealing a special porthole along the side of the endovascular stent to allow placement of a catheter for embolization and diagnostic purposes.
Figure 12A:
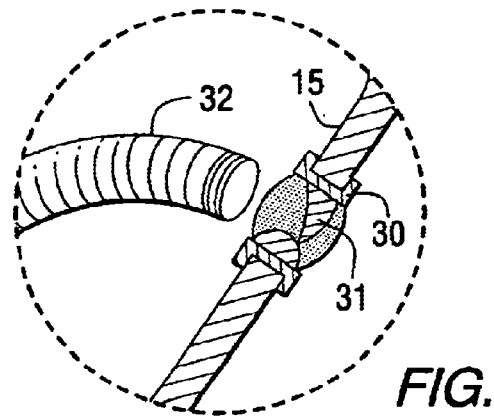

As shown in FIG. 12, a special radiopaque port 30 can be made along the side of the mid-section 15. The port 30 may include a one-way valve 31. The one-way valve 31 is structured to allow a catheter 32 to pass therethrough. The valve 31 allows the passage of embolic materials such as glue as well as the passage of microcatheters for specialized embolization.

Figure 13:
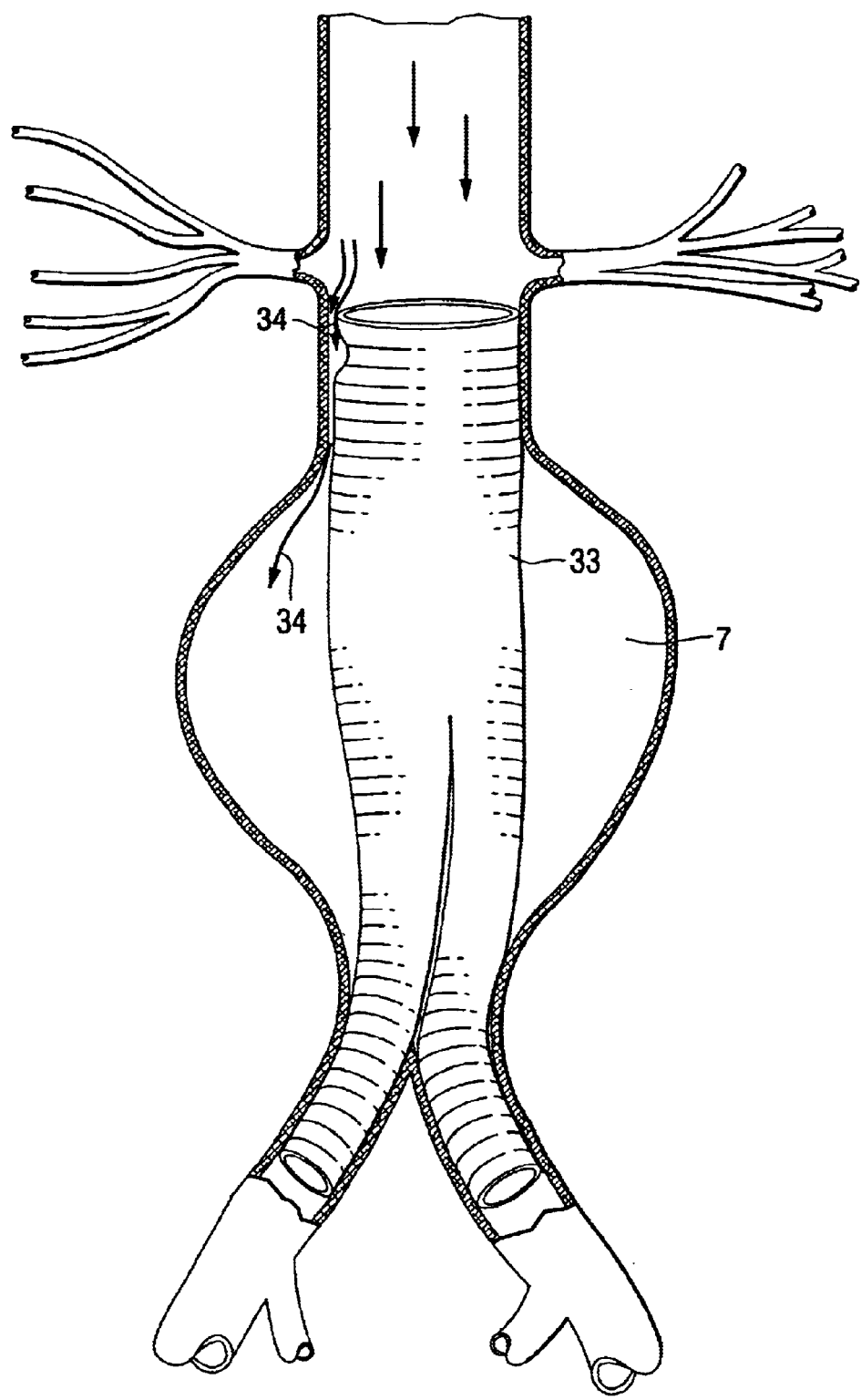
FIG. 13 is an illustration of a modular stent graft being deployed at the level of the renal arteries. The stent graft is shown in a cross-sectional view of the human abdominal aorta. Blood coming caudally is going around the cranial end of the stent graft forming an endoleak.
Figure 14:
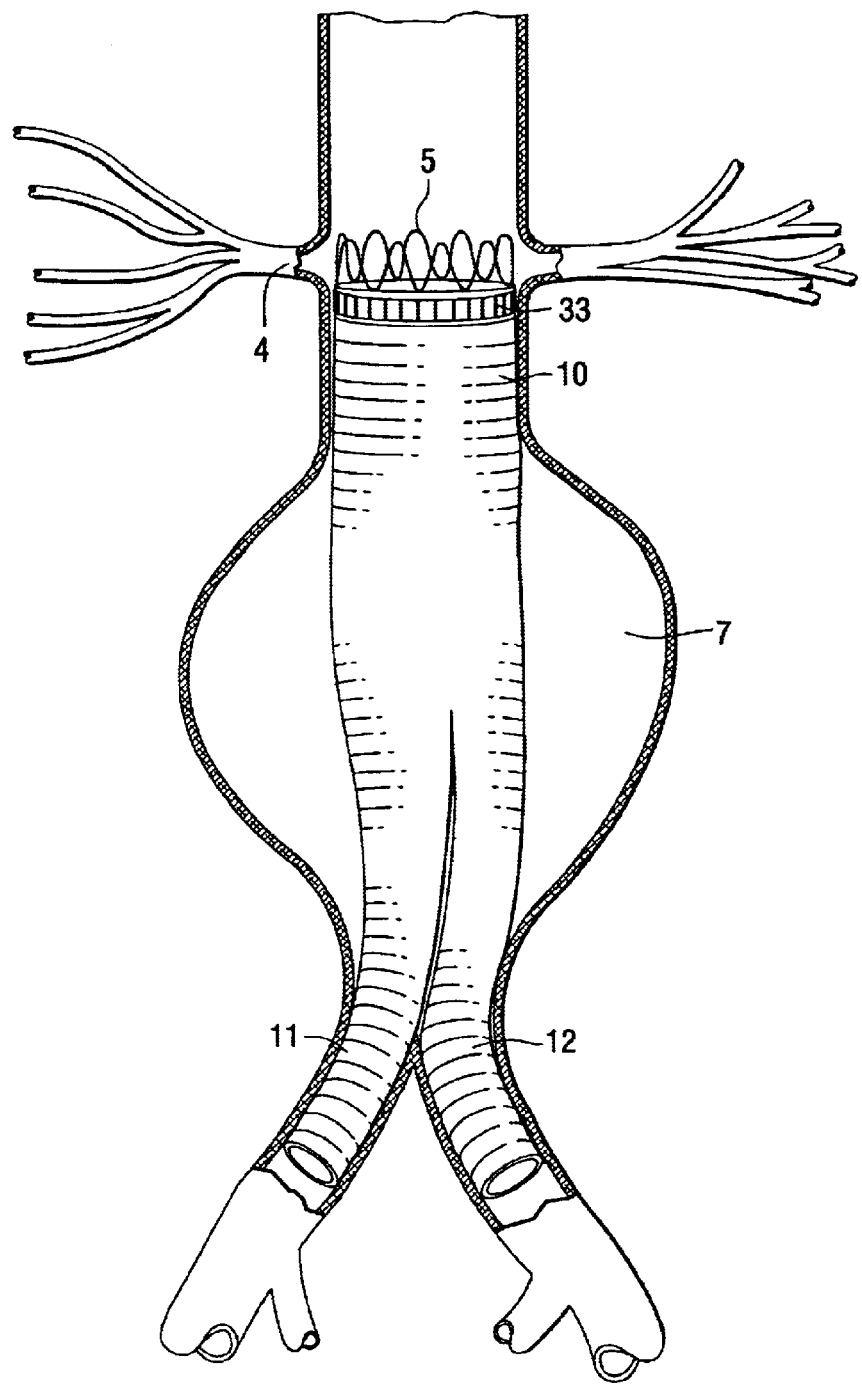
FIG. 14 is an illustration of a modular stent graft being deployed at the level of the renal arteries with the endovascular stent placed cranially. The endovascular stent with its uncovered struts project over the ostiums of the renal arteries and other branches; this helps to provide support for the endovascular stent. The endovascular stent provides radial strength against the modular stent graft which will help prevent endoleaks.
Figure 15:
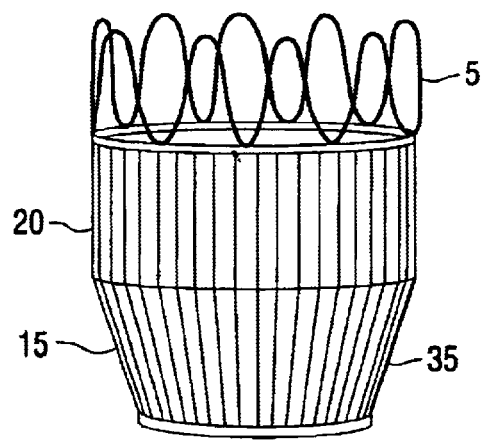
FIG. 15 is a slight oblique lateral view of an alternate embodiment.

FIGS. 13–16 shows an additional method of using the invention to aid in reducing or preventing endoleaks. That is, to prevent fluid from leaking around a previously installed stent 33. As shown in FIG. 13, a previously installed stent 33 may not seat properly or may degrade over time thereby allowing endoleaks 34. Such a leak allows fluid to pass around the previously installed stent 33 and into the aneurysm 7. The endovascular stent 1 may be inserted into the previously installed stent 33 to provide additional support so that endoleaks 34 are reduced or prevented. As shown in FIG. 14, because struts 5 permit fluid to flow therethrough, the struts 5 may extend beyond the perimeter of the prior stent 33 and over the ostiums 4 of the renal arteries other important branch vessels. As shown in FIG. 15, the endovascular stent 35 may include only the cephalic section 13 and the mid-section 15. In this configuration, the endovascular stent 35 provides radial strength against the wall of the cranial component of the prior stent graft 33, which is then biased against the wall of the aorta, thus, preventing endoleaks.

Figure 16:
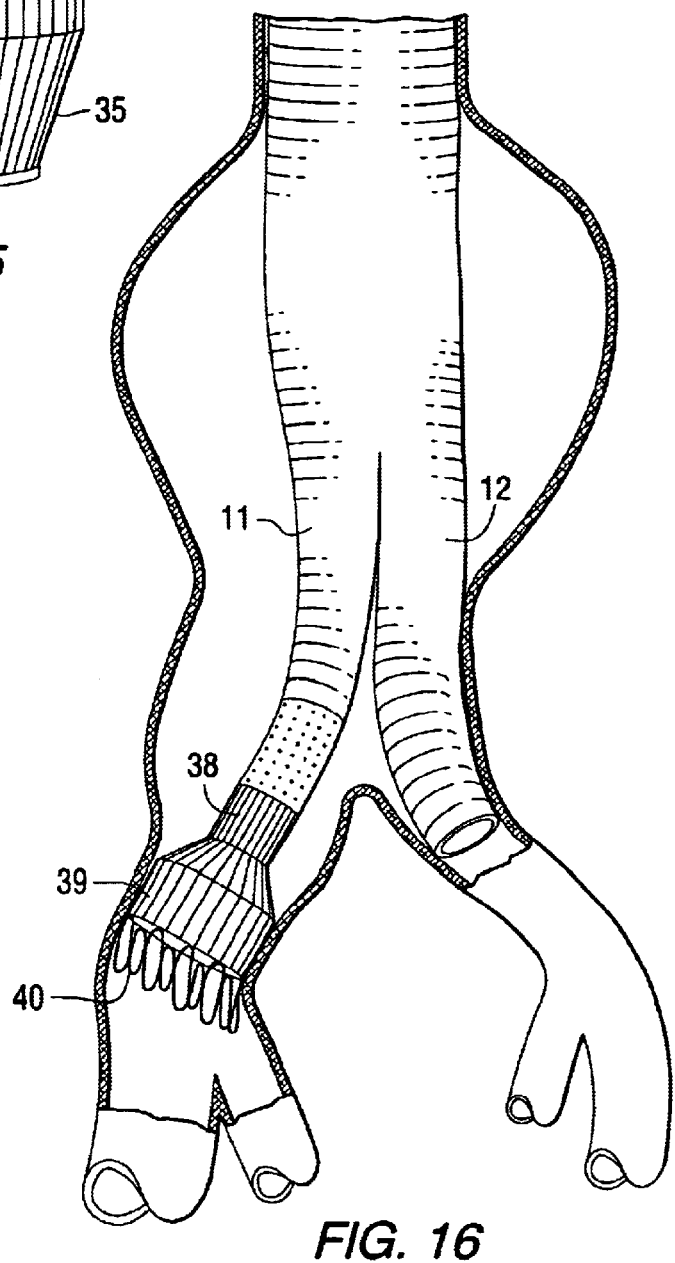
FIG. 16 is an illustration of a cross sectional view of the abdominal aortic aneurysm extending into the right common iliac artery. The endovascular stent is inserted into the right limb of the modular stent system to seal the large aneurysm.

The endovascular stent 1 may also be used as shown in FIG. 16. In this embodiment, the endovascular stent 1 is an inverted orientation and coupled to the caudal end of the modular sent graft 8. In such a configuration the endovascular stent 1 is used to treat an iliac aneurysm 37. Because the endovascular stent 1 is inverted, the terms used to identify the respective ends, i.e. cephalic section 13 and caudal section 17, are no longer appropriate. When used in the inverted position, what was identified as the cephalic section 13 is now identified as the flared end 39 and what was identified as the caudal section 17 is now identified as the narrow end 38. The flared end 38 includes the covering 20 which forms a flared end lumen 40. The narrow end also includes the covering 20 which forms the narrow end lumen 42. The flared end 39 projects caudally, or into the aneurysm, and engages the normal iliac artery wall. A noncovered strut section 40 may be used to provide for additional support. The narrow end 39 is coupled to the modular sent graft 8. Preferably, the modular sent graft 8 projects into and engages the narrow end lumen 42.

While specific embodiments of the invention have been described in detail, it will be appreciated by those skilled in the art that various modifications and alternatives to those details could be developed in light of the overall teachings of the disclosure. For example, the internal attachment hooks 27 could be utilized on an endovascular stent 1' having hooks 26. Similarly, the endovascular stent 1' could be formed with exposed struts 5. Accordingly, the particular arrangements disclosed are meant to be illustrative only and not limiting as to the scope of invention which is to be given the full breadth of the claims appended and any and all equivalents thereof.

What is claimed is:

1. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and wherein the caudal section defines a caudal lumen and has a cross-sectional area smaller than the cross-sectional area of the cephalic section; and
   a tapered mid-section attached to said cephalic section and said caudal section, wherein said caudal section is connected to said cephalic section and said mid-section surrounds said connection between said caudal section and said cephalic section.

2. The endovascular stent of claim 1 wherein said caudal section is structured to be attached to a secondary stent graft.

3. The endovascular stent of claim 1 wherein:
   said cephalic section, mid-section, and caudal section include a frame; and
   at least a portion of said cephalic section, mid-section, and caudal section frame has a covering.

4. The endovascular stent of claim 3 wherein a portion of the cephalic section is uncovered.

5. The endovascular stent of claim 4 wherein said cephalic section, mid-section, and caudal section frame is an integral frame.

6. The endovascular stent of claim 5 wherein said frame and said cover are structured to have an expanded configuration and an unexpanded configuration.

7. The endovascular stent of claim 6 wherein said frame includes a plurality of helically arranged undulating members containing multiple turns about a common longitudinal axis.

8. The endovascular stent of claim 7 wherein said frame is biased radially outward at said cephalic section to seal against the vessel wall and is biased radially inward at said caudal section to seal against a second stent graft when said frame is in said expanded configuration.

9. The endovascular stent of claim 8 wherein said undulating members are generally U-shaped and overlap each other in a forward and backward manner along the longitudinal axis.

10. The endovascular stent of claim 9 wherein said undulating members are overlapping on each other in a crisscross manner along a longitudinal axis.

11. The endovascular stent of claim 10 wherein said frame and cover are structured to cooperate with a balloon structured to expand said frame and cover from said unexpanded configuration to said expanded configuration.

12. The endovascular stent of claim 11 wherein said frame is constructed of a memory metal composition.

13. The endovascular stent of claim 3 wherein said covering includes a coating to aid in cell growth.

14. The endovascular stent of claim 13 wherein:
said cephalic section cross-sectional area in an expanded position is about 800 to about 1,200 $mm^2$; and
said caudal section cross-sectional area in an expanded position is about 300 to about 600 $mm^2$.

15. The endovascular stent of claim 13 wherein:
said cephalic section has a diameter in an expanded position of about 35 mm; and
said caudal section has a diameter in an expanded position of about 24 mm.

16. The endovascular stent of claim 13 wherein said caudal section includes a plurality of protruding structures along an inner surface which is structured to engage a plurality of protruding structures on a secondary stent graft.

17. The endovascular stent of claim 1 wherein said covering is polytetrafluoroethylene.

18. The endovascular stent of claim 1 wherein:
said cephalic section cross-sectional area in an expanded position is about 800 to 1,200 $mm^2$; and
said caudal section cross-sectional area in an expanded position is about 300 to 600 $mm^2$.

19. The endovascular stent of claim 1 wherein:
said cephalic section has a diameter in an expanded position of about 35 mm; and
said caudal section has a diameter in an expanded position of about 24 mm.

20. The endovascular stent of claim 1 wherein said cephalic section, mid-section, and caudal section include a plurality of radiopaque markers.

21. The endovascular stent of claim 1 wherein said cephalic section includes a plurality of protruding structures along a outer surface that will engage a vessel wall.

22. The endovascular stent of claim 1 wherein said caudal section includes a plurality of protruding structures along an inner surface which is structured to engage a plurality of corresponding structures on a secondary stent graft.

23. The endovascular stent of claim 1, comprising at least one one-way valve extending form an interior portion to an exterior portion of the stent structured to allow for the injection of materials outside the said stent graft and into a space occupied by an abdominal aortic aneurysm.

24. A method of using an endovascular stent having a different sized cylindrical end sections and a tapered section therebetween for treating a distal iliac aneurysm, said method comprising the steps of:
providing a collapsible endovascular stent having a flared section having a cross-sectional area, a narrow section having a cross-sectional area smaller than the cross-sectional area of the flared section, and a tapered mid-section attached to said flared section and said narrow section;
collapsing said endovascular stent into a collapsed configuration;
inserting said endovascular stent into a patient with a vascular sheath to a location within an iliac artery adjacent to a iliac aneurysm; and
expanding said endovascular stent to an expanded configuration wherein said flared section engages the iliac artery.

25. The method of claim 24 comprising the further steps of:
providing a stent graft having a medial limb and lateral limb;
inserting said stent graft in a patient within the abdominal aorta; and
attaching said endovascular stent either to said medial limb or lateral limb.

26. The method of claim 24, wherein the narrow section does not expand against the entire aneurysm.

27. An endovascular stent system comprising:
a generally cylindrical cephalic section defining a cephalic lumen and having a cross-sectional area;
a caudal section defining a caudal lumen and having a cross-sectional area smaller than the cross-sectional area of the cephalic section;
a tapered mid-section attached to said cephalic section and said caudal section;
a secondary stent graft attached to said caudal section; and
wherein said caudal section is unwardly radially biased against said secondary stent graft and includes a plurality of protruding structures along an inner surface which are structured to engage a plurality of corresponding structures on the secondary stent graft.

28. The endovascular stent system of claim 27 wherein:
said cephalic section, mid section, and caudal section include a frame; and
at least a portion of said cephalic section, mid-section, and caudal section frame has a covering.

29. The endovascular stent system of claim 27 wherein a portion of the cephalic section is uncovered.

30. The endovascular stent system of claim 28 wherein said frame and said cover are structured to have an expanded configuration and an unexpanded configuration.

31. The endovascular stent system of claim 30 wherein said frame includes a plurality of helically arranged undulating members containing multiple turns about a common longitudinal axis.

32. The endovascular stent system of claim 31 wherein said frame is biased radially outward at said cephalic section to seal against the vessel wall and is biased radially inward at said caudal section to seal against the secondary stent graft when said frame is in said expanded configuration.

33. The endovascular stent system of claim 31 wherein said undulating members are generally U-shaped and overlap each other in a forward and backward manner along the longitudianal axis.

34. The endovascular stent system of claim 31 wherein said undulating members are overlapping on each other in a crisscross manner along a longitudinal axis.

35. The endovascular stent system of claim 34 wherein said frame and cover are structured to cooperate with a balloon structure to expand said frame and cover from said unexpanded configuration to said expanded configuration.

36. The endovascular stent system of claim 35 wherein said frame is constructed of a memory metal composition.

37. The endovascular stent system of claim 27 wherein said caudal section is connected to said cephalic section and said mid-section surrounds said connection between said caudal section and said cephalic section.

38. The endovascular stent system of claim 27 wherein said cephalic section includes a plurality of protruding structures along an outer surface that will engage a vessel wall.

39. The endovascular stent system of claim 27, comprising at least one one-way valve extending from an interior portion to an exterior portion of the stent structured to allow for the injection of materials outside the said stent graft and into a space occupied by an abdominal aortic aneurysm.

40. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and wherein the caudal section defines a caudal lumen and has a cross-sectional area smaller than the cross-sectional area of the cephalic section;
   a tapered mid-section attached to said cephalic section and said caudal section,
   wherein said cephalic section, mid-section, and caudal section include an integral frame, at least a portion of said cephalic section, mid section, and caudal section frame has a covering, and a portion of the cephalic section is uncovered, said frame and said cover are structured to have an expanded configuration and an unexpanded configuration, said frame includes a plurality of helically arranged undulating members containing multiple turns about a common longitudinal axis, and said frame is biased radially outward at said cephalic section to seal against the vessel wall and is biased radially inward at said caudal section to seal against a second stent graft when said frame is in said expanded configuration.

41. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and the caudal section defines a caudal lumen having a cross-sectional area smaller than the cross-sectional area of the cephalic section; and
   a tapered mid-section attached to said cephalic section and said caudal section, wherein said caudal section is connected to said cephalic section and said mid-section surrounds said connection between said caudal section and said cephalic section.

42. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, wherein the caudal section defines a caudal lumen and has a cross-sectional area smaller than the cross-sectional area of the cephalic section; and
   a tapered mid-section attached to said cephalic section and said caudal section, wherein said cephalic section cross-sectional area in an expanded position is about 800 to 1,200 $mm^2$, and said caudal section cross-sectional area in an expanded position is about 300 to 600 $mm^2$.

43. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and wherein the caudal section defines a caudal lumen and has a cross-sectional area smaller than the cross-sectional area of the cephalic section; and
   a tapered mid-section attached to said cephalic section and said caudal section, wherein said cephalic section has a diameter in an expanded position of about 35 mm, and said caudal section has a diameter in an expanded position of about 24 mm.

44. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and wherein the caudal section defines a caudal lumen and has a cross-sectional area smaller than the cross-sectional area of the cephalic section; and
   a tapered mid-section attached to said cephalic section and said caudal section, wherein said caudal section includes a plurality of protruding structures along an inner surface which is structured to engage a plurality of corresponding structures on a secondary stent graft.

45. An endovascular stent comprising:
   a generally cylindrical cephalic section structured and configured to expand against a wall of a blood vessel, wherein the cephalic section defines a cephalic lumen and has a cross-sectional area;
   a caudal section structured and arranged to be inserted into at least a portion of an aneurysm of the blood vessel, wherein the caudal section does not expand against the entire aneurysm when placed into the aneurysm, and wherein the caudal section defines a caudal lumen and has a cross-sectional area smaller than the cross-sectional area of the cephalic section;
   a tapered mid-section attached to said cephalic section and said caudal section, wherein said cephalic section, mid-section, and caudal section are an integral frame having a plurality of helically arranged undulating members containing multiple turns about a common longitudianal axis, said frame is biased radially outward at said cephalic section to seal against the vessel wall and is biased radially inward at said caudal section to seal against a second stent graft when said frame is in said expanded configuration; and at least a portion of said cephalic section, mid-section, and caudal section frame has a covering, such that a portion of the cephalic section is uncovered, said covering includes a coating to aid in cell growth, said frame and said cover are structured to have an expanded configuration and an unexpanded configuration.

46. The endovascular stent of claim 45 wherein said undulating members are generally U-shaped and overlap each other in a forward and backward manner along the longitudinal axis.

47. The endovascular stent of claim 46 wherein said undulating members are overlapping on each other in a crisscross manner along a longitudinal axis.

48. The endovascular stent of claim 47 wherein said frame and cover are structured to cooperate with a balloon structured to expand said frame and cover from said unexpanded configuration to said expanded configuration.

49. The endovascular stent of claim 48 wherein said frame is constructed of a memory metal composition.

* * * * *

UNITED STATES PATENT AND TRADEMARK OFFICE
CERTIFICATE OF CORRECTION

| | | |
|---|---|---|
| PATENT NO. | : 6,773,454 B2 | Page 1 of 1 |
| APPLICATION NO. | : 09/753119 | |
| DATED | : August 10, 2004 | |
| INVENTOR(S) | : Michael H. Wholey, Mark H. Wholey and Boulos Toursarkissian | |

It is certified that error appears in the above-identified patent and that said Letters Patent is hereby corrected as shown below:

On Title page
(*)Notice and item 45
Patent Term Adjustment under 35 U.S.C. 154(b) is by 0 days.
Notification dated July 22, 2004, states the Patent Term Adjustment is 31 days.

Column 4, Line 60
"is structured to prevent leakage, rupture of" should read -- is structured to prevent leakage, rupture or --

Column 6, Line 63 (Claim 5)
"and caudal section frame is an integral" should read -- and caudal section is an integral --

Column 7, Line 62 (Claim 23)
"one one-way valve extending form" should read -- one one-way valve extending from --

Column 8, Line 37 (Claim 27)
"wherein said caudal section is unwardly" should read -- wherein said caudal section is inwardly --

Signed and Sealed this

Twenty-third Day of October, 2007

JON W. DUDAS
*Director of the United States Patent and Trademark Office*